United States Patent
Richardson et al.

(10) Patent No.: US 10,005,665 B2
(45) Date of Patent: Jun. 26, 2018

(54) METHODS AND SYSTEMS FOR PRODUCING HIGH PURITY GASEOUS CHLORINE DIOXIDE

(71) Applicant: CHEMTREAT, INC., Glen Allen, VA (US)

(72) Inventors: John Richardson, Hanover, VA (US); Kevin White, Richmond, VA (US); Benjamin Niemaseck, Chesterfield, VA (US); Douglas McIlwaine, Ashland, VA (US); James Wilkins, Midlothian, VA (US)

(73) Assignee: CHEMTREAT, INC., Glen Allen, VA (US)

( * ) Notice: Subject to any disclaimer, the term of this patent is extended or adjusted under 35 U.S.C. 154(b) by 258 days.

(21) Appl. No.: 14/878,603

(22) Filed: Oct. 8, 2015

(65) Prior Publication Data

US 2016/0251219 A1  Sep. 1, 2016

Related U.S. Application Data

(60) Provisional application No. 62/121,173, filed on Feb. 26, 2015.

(51) Int. Cl.
  *C01B 11/02* (2006.01)
(52) U.S. Cl.
  CPC .................. *C01B 11/024* (2013.01)
(58) Field of Classification Search
  CPC .................................................... C01B 11/024
  See application file for complete search history.

(56) References Cited

U.S. PATENT DOCUMENTS

| | | | |
|---|---|---|---|
| 4,504,442 A | 3/1985 | Rosenblatt et al. | |
| 5,290,524 A | 3/1994 | Rosenblatt et al. | |
| 5,476,579 A | 12/1995 | Choi et al. | |
| 6,537,821 B1 | 3/2003 | Rosenblatt et al. | |
| 6,716,354 B2 | 4/2004 | Rosenblatt et al. | |
| 6,824,756 B2 | 11/2004 | Rosenblatt et al. | |
| 6,841,053 B2 * | 1/2005 | Winquist | G01N 33/0039 204/406 |
| 7,964,138 B2 | 6/2011 | Richardson et al. | |
| 8,323,563 B2 | 12/2012 | Richardson et al. | |
| 2002/0125196 A1 | 9/2002 | Rosenblatt et al. | |

(Continued)

FOREIGN PATENT DOCUMENTS

| | | |
|---|---|---|
| GB | 746615 A | 3/1956 |
| WO | 2008/090367 A1 | 7/2008 |
| WO | 2010/019491 A1 | 2/2010 |

OTHER PUBLICATIONS

Nov. 4, 2016 International Preliminary Report on Patentability issued in International Patent Application No. PCT/US16/16771.

(Continued)

*Primary Examiner* — Ngoc-Yen Nguyen
(74) *Attorney, Agent, or Firm* — Oliff PLC

(57) ABSTRACT

Methods and systems for producing high purity gaseous chlorine dioxide are provided. A solid chlorite reactant is contacted with an ozone-containing reactant gas, or a gas containing both ozone and a component that reacts with any hydroxide byproduct (such as carbon dioxide), to produce chlorine dioxide. The reaction can be monitored and controlled to ensure that excess chlorite reactant is provided and to prevent ozone from passing into the product gas.

18 Claims, 5 Drawing Sheets

(56) References Cited

U.S. PATENT DOCUMENTS

| | | |
|---|---|---|
| 2003/0138371 A1 | 7/2003 | McWhorter et al. |
| 2003/0215381 A1 | 11/2003 | Rosenblatt et al. |
| 2004/0258607 A1 | 12/2004 | Rosenblatt et al. |
| 2004/0259188 A1 | 12/2004 | Rosenblatt et al. |
| 2005/0019210 A1 | 1/2005 | Rosenblatt et al. |
| 2005/0109695 A1* | 5/2005 | Olivier ............ A01K 63/04 210/605 |
| 2007/0178021 A1 | 8/2007 | McWhorter et al. |
| 2007/0183961 A1 | 8/2007 | McWhorter et al. |
| 2008/0026029 A1* | 1/2008 | Wellinghoff .......... A01N 3/02 424/408 |
| 2008/0139869 A1 | 6/2008 | Wilson et al. |
| 2008/0286147 A1 | 11/2008 | Wilson et al. |
| 2009/0142226 A1 | 6/2009 | McWhorter et al. |
| 2009/0159538 A1 | 6/2009 | Duve |
| 2010/0209528 A1 | 8/2010 | McWhorter et al. |
| 2011/0236257 A1* | 9/2011 | Sumner ............ A01N 59/00 422/37 |
| 2012/0131887 A1 | 5/2012 | McWhorter et al. |
| 2012/0135167 A1 | 5/2012 | McWhorter et al. |
| 2012/0148477 A1 | 6/2012 | Rosenblatt et al. |
| 2012/0201898 A1 | 8/2012 | McWhorter et al. |
| 2012/0201899 A1 | 8/2012 | McWhorter et al. |
| 2014/0113007 A1 | 4/2014 | Kato et al. |

OTHER PUBLICATIONS

Apr. 15, 2016 International Search Report issued in International Patent Application No. PCT/US2016/016771.

Apr. 15, 2016 Written Opinion of the International Searching Authority issued in International Patent Application No. PCT/US2016/016771.

Masschelein, et al. "Chlorine Dioxide—Chemistry and Environmental Impact of Oxychlorine Compounds," Ann Arbor Science, 1979, pp. 35-37.

\* cited by examiner

METHODS AND SYSTEMS FOR PRODUCING HIGH PURITY GASEOUS CHLORINE DIOXIDE

CROSS REFERENCE TO RELATED APPLICATION

This application claims priority to U.S. Provisional Application No. 62/121,173 filed on Feb. 26, 2015, the content of which is incorporated by reference herein in its entirety.

BACKGROUND

Chlorine dioxide is widely used in industrial applications. It can be used as a disinfecting agent in potable water and wastewater treatment processes. It can also be used as a bleaching agent in the production of wood pulp, paper, oils, and flour.

Chlorine dioxide is difficult to stably and safely transport, and thus is most often generated on-site (i.e., at the plant or facility in which it is used). Traditional methods for producing chlorine dioxide use a liquid reactant solution. These methods typically involve reacting a chlorite with an acid or reacting chlorate with a reducing agent and an acid in solution. These liquid-based reactions can be inefficient and typically produce a product with significant levels of impurities, such as chloride, chlorate, and sulfate. Additionally, on-site storage of strong acids poses significant hazards and regulatory hurdles. Pure chlorine dioxide can be produced by employing gas stripping techniques. However, this involves additional costs and facilities and generally overcomplicates the manufacturing processes.

Other methods for producing chlorine dioxide involve solid phase-gas phase reactions. These reactions typically produce relatively pure chlorine dioxide by reacting solid sodium chlorite with highly reactive chlorine gas. Chlorine gas is extremely hazardous and difficult to handle. As such, these methods for producing chlorine dioxide are expensive and burdensome to integrate into manufacturing facilities due to the required regulatory and safety procedures.

SUMMARY

In one aspect, it was discovered that high purity gaseous chlorine dioxide can be produced by a safe and convenient method that reacts solid chlorite and gaseous ozone. Ozone is a relatively safe, feasible alternative to chlorine gas. Ozone is stable when mixed with other gases such as those found in air, including nitrogen, oxygen, and carbon dioxide, and the presence of water vapor does not substantially impair the reaction. It was also discovered that production of high purity gaseous chlorine dioxide can be increased by reacting solid chlorite with gaseous ozone in the presence of carbon dioxide. Embodiments of the invention can provide the following features and benefits:

1. highly pure chlorine dioxide can produced;
2. substantially no chlorite ions, chlorate ions, perchlorate ions, or molecular chlorine are generated in the final product;
3. the system and methods are low cost, safe, simple, and reliable;
4. turndown across the entire operating range may be performed without compromising purity;
5. true flow pacing may be obtained, without recalibration, adjustment, or operator intervention;
6. the reactor has a small equipment footprint;
7. standard equipment modules can be custom configured; and
8. no bulk storage of liquid chemicals is needed.

In one aspect, this disclosure relates to a method of producing gaseous chlorine dioxide by contacting a solid chlorite reactant with an ozone-containing gas and reacting ozone with the chlorite reactant to produce the gaseous chlorine dioxide. The ozone may be reacted with the chlorite reactant in the presence of carbon dioxide to increase the amount of gaseous chlorine dioxide produced.

In another aspect, this disclosure relates to a system for producing gaseous chlorine dioxide. The system can include an ozone generator that is configured to produce an ozone-enriched gas, and a reactor that includes solid chlorite reactant and is configured to (i) receive the ozone-enriched gas from the ozone generator and (ii) exhaust a gas product including gaseous chlorine dioxide that is produced from reacting the solid chlorite reactant with ozone in the ozone-enriched gas.

Additional embodiments and features are described in the detailed description that follows.

DETAILED DESCRIPTION OF EMBODIMENTS

Figure 1:
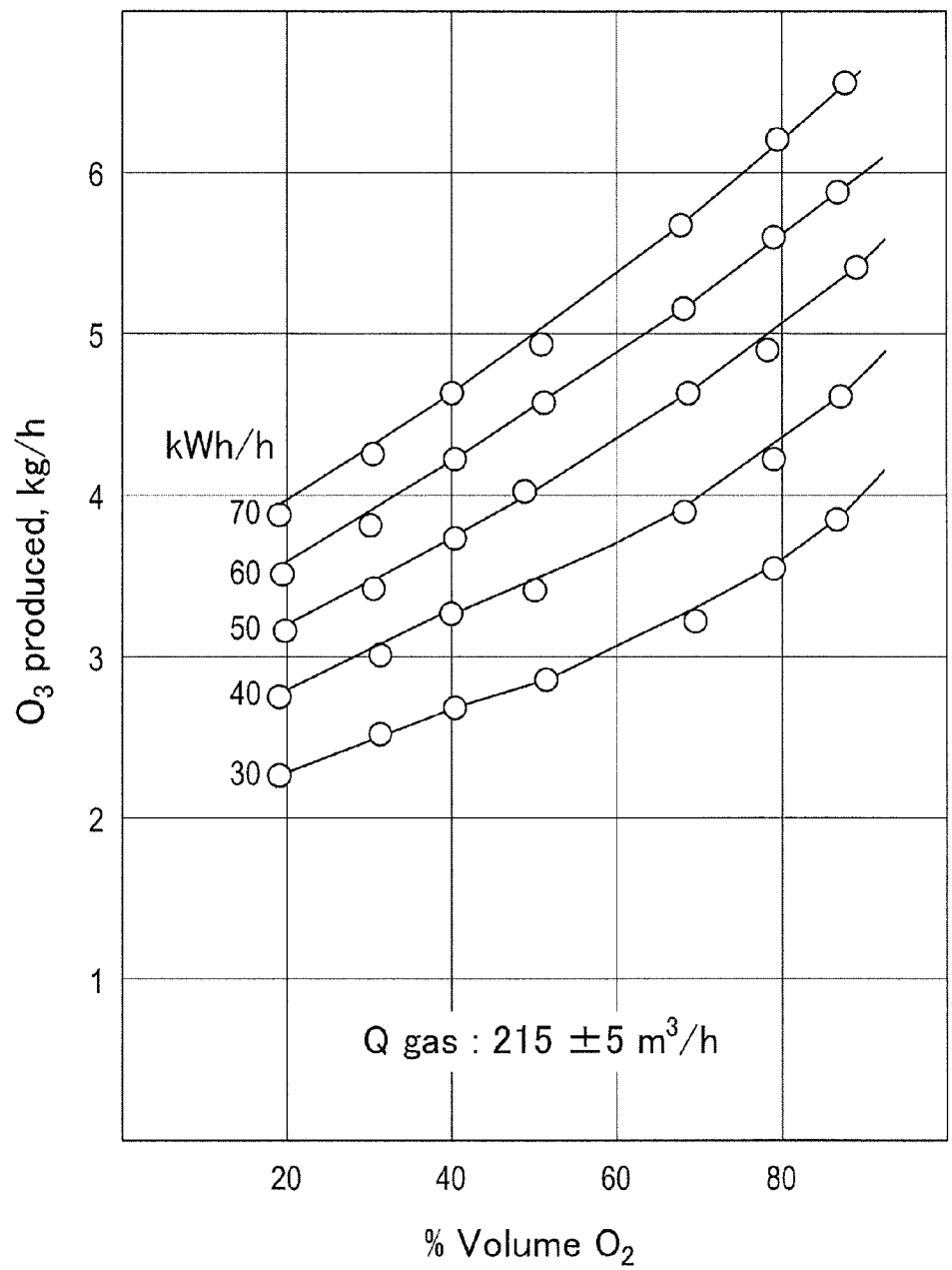
FIG. 1 is a graph showing ozone production as a function of oxygen levels.

As described herein, systems and methods for producing chlorine dioxide gas are provided. The systems and methods include reacting gaseous phase ozone with solid chlorite media to produce gaseous chlorine dioxide. An ozone gas source feeds gaseous phase ozone into a point of contact with a surface of the solid chlorite media. The ozone gas reacts with the surface of the solid chlorite media to form chlorine dioxide gas. The gaseous chlorine dioxide may then be dissolved in water and used or stored for future use. Alternatively, the gaseous chlorine dioxide may be directly deposited into a receiving stream of an industrial process.

The systems and methods also include reacting gaseous phase ozone with solid chlorite media in the presence of carbon dioxide to produce gaseous chlorine dioxide. A first gas stream containing gaseous phase ozone and a second gas stream containing carbon dioxide can be combined to form a reactant gas that is exposed to a surface of the solid chlorite media. The ozone in the reactant gas reacts with the surface of the solid chlorite media to form chlorine dioxide gas.

As explained below, the systems and methods can incorporate various techniques for monitoring and controlling the reaction.

Methods are provided for producing highly pure chlorine dioxide gas by reacting gaseous phase ozone with solid phase chlorite material. In one embodiment, ozone gas is reacted with solid phase sodium chlorite to form chlorine dioxide gas. In a possible reaction mechanism, the reaction additionally forms an ozonide byproduct. For example, the reaction may proceed as follows:

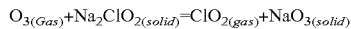

$$O_{3(Gas)} + Na_2ClO_{2(solid)} = ClO_{2(gas)} + NaO_{3(solid)}$$

Without intending to be bound by theory, it is believed that the typical reaction of gaseous phase ozone with solid phase chlorite material produces both gaseous phase chlorine dioxide and a solid phase sodium ozonide byproduct. The sodium ozonide byproduct eventually decomposes into sodium hydroxide and oxygen gas. A small amount of sodium peroxide may also be produced as a byproduct of this reaction. Sodium peroxide may be observed as a yellow/orange solid byproduct. However, this byproduct appears to decompose and the color disappears.

The ozone gas can be provided in an ozone gas source (an ozone-containing gas) optionally containing other gases. Carbon dioxide can be added to the ozone gas source prior to introducing the ozone gas source to the solid phase chlorite material, or can be introduced separately to the reaction vessel or at the point of contact with the solid phase chlorite material.

For example, oxygen may be fed through an ozone generator, converting some of the oxygen to ozone. Carbon dioxide may then be added to the resulting ozone gas source (containing both oxygen and ozone) to provide a reactant gas containing oxygen, ozone, and carbon dioxide. The reactant gas can then be introduced to the solid chlorite media in a reaction vessel; upon contact, the ozone in the reactant gas will react with the solid chlorite media to form chlorine dioxide gas. The chlorine dioxide gas exits the reaction vessel together with the oxygen (if present) and any remaining carbon dioxide.

Alternatively, the carbon dioxide may be added to the ozone gas source at the reaction vessel or at the point of contact with the solid phase chlorite material. In this case, a gas stream containing the ozone gas source and a gas stream containing carbon dioxide are separately introduced to the reaction vessel, forming a combined reactant gas in the reaction vessel in which the solid chlorite media is present. The ozone in the reactant gas will react with the solid chlorite media to form chlorine dioxide gas in the presence of the carbon dioxide.

As described above, the ozone reacts with the solid chlorite media to produce gaseous phase chlorine dioxide and, where sodium chlorite is used, a solid phase sodium ozonide byproduct. The sodium ozonide byproduct eventually decomposes into sodium hydroxide and oxygen gas. A small amount of sodium peroxide may also be produced as a byproduct of this reaction. In the presence of carbon dioxide, the sodium hydroxide and any sodium peroxide are converted to sodium carbonate, which is safe to handle. Other components may be added to the reaction vessel to react with the sodium hydroxide and/or sodium peroxide to eliminate or reduce those components in the reaction vessel.

Although not necessary for the production of chlorine dioxide, the inclusion of carbon dioxide in the reactant gas can lead to significantly higher yield. The effect is more pronounced when oxygen gas (rather than air) is used to produce the ozone. Without intending to be bound by theory, it is believed that the carbon dioxide promotes contact between the solid chlorite media and the ozone, allowing the ozone to effectively penetrate the chlorite material and thereby promote further reaction and production of chlorine dioxide. It is believed that when sodium chlorite is reacted with ozone in the absence of carbon dioxide, the sodium hydroxide reaction product forms a protective gloss over the sodium chlorite, inhibiting complete reaction between the sodium chlorite and the ozone. By contrast, the sodium chlorite remains exposed to the ozone when carbon dioxide is present in the reactant gas.

The ozone gas source may be provided by any suitable means as long as ozone is present in the reactant stream at a minimum threshold amount. For example, ozone may be derived from a pre-manufactured ozone gas source stored in a storage vessel. Ozone may also be provided by an ozone generator using conventional ozone generation methods such as those employed by ultraviolet (UV) light generators, corona discharge generators, or cold plasma generators. These generators are merely illustrative of the available techniques for generating ozone, however, and are not intended to limit the scope of the invention.

Generally, ozone generators produce ozone by converting $O_2$ into $O^-$ ions, which react with $O_2$ to form $O_3$. Ozone generation systems can require an oxygen-containing gas source, and the concentration of oxygen within the oxygen-containing gas source can impact the production rate of ozone. Other factors include humidity, purity, and temperature of the oxygen-containing gas. These parameters should be optimized according to which ozone generation system is used. The oxygen containing gas source may be fed to the ozone generators from a variety of sources including ambient air (containing approximately 23 wt. % oxygen) or purified oxygen (containing approximately 95 wt. % oxygen), the latter of which can be produced by an oxygen generator. The oxygen-containing gas source that is fed to the ozone generators can have an oxygen concentration range preferably of from 10-100 wt. %, and more preferably of from 60-100 wt. %, and more preferably of from 80-100 wt. %, and more preferably of from 90-100 wt. %, and even more preferably of from 95-100 wt. %.

In UV light generation techniques for producing ozone, a UV lamp emitting light at a wavelength of less than 240 nm is used to convert $O_2$ into $O_3$. UV light generation is inexpensive and is beneficial for smaller systems requiring lower quantities of ozone. FIG. 1 shows an ozone production curve from a UV light ozone generator. As illustrated in FIG. 1, ozone production increases with an increase in the oxygen concentration of the oxygen-containing gas source. Ozone production also increases with an increase of the kWh/h of the UV light ozone generator.

Corona discharge (CD) generation produces ozone by passing a cold dry oxygen-containing gas through an electrical field. There are three types of CD generation: low frequency generation (50 to 100 Hz), medium frequency generation (100 to 1000 Hz), and high frequency generation (1,000+ Hz). The oxygen source feeding a CD generator is preferably substantially void of moisture, as moisture can cause nitric acid production, which can lead to the corrosion of a CD generator's internal mechanisms. Additionally, CD generators require a cool air to efficiently produce ozone.

Of the ozone technologies mentioned above, none has a clear advantage, and any known system for generating ozone can be variously incorporated into the systems and methods disclosed herein if needed. The determination as to which ozone gas source to use is determined by a number of factors, including the rate of ozone gas production, cost, physical footprint, ease of integration, and the source of the oxygen-containing gas.

The ozone gas derived from these sources may be propelled or exhausted by conventional means into the reaction area through piping or tubing.

An ozone generator can provide an ozone production capacity ranging from 0.001-100 Kg/hr, from 0.05-50 Kg/hr, from 0.5-20 Kg/hr, and from 1-10 Kg/hr. Although a specific concentration of ozone gas is not needed to produce gaseous chlorine dioxide, the ozone should be provided in a sufficient concentration so that the reaction initiates and generates the desired amounts of chlorine dioxide. For example, the gas reactant stream may include ozone in a concentration ranging from 5 ppm to 250,000 ppm, from 10 ppm to 100,000 ppm, from 250 ppm to 10,000 ppm, or from 500 ppm to 5,000 ppm. The amount of chlorine dioxide produced is a function of a variety of parameters including the concentration of ozone reacted with the solid chlorite material.

The amount of ozone provided in the reaction may be controlled by ozone destruction such as through the use of ozone destructors, which break down ozone present in the system. Ozone destructors are useful in terminating the reaction and preventing excess consumption of the chlorite media by eliminating excess ozone present in the system. Ozone destructors may be in the form of a catalyst, such as magnesium oxide, for example. Other ozone destructors can be used.

The ozone is reacted by passing the reactant gas over solid phase chlorite reactant media. The solid phase chlorite reactant can be included in a reactor such as a packed bed, a column, a drum, or the like. The ozone containing reactant stream (which may also include carbon dioxide) can be fed into one end of the reactor, and the gaseous chlorine dioxide product can be taken from the other end of the reactor. In this configuration, the pressure from the reactant gas pushes the chlorine dioxide product gas through the reactor and substantially prevents the ozone from mixing with the chlorine dioxide. Ozone can react with the chlorine dioxide product to degrade the chlorine dioxide and produce unwanted byproducts. The reactor is preferably configured so that the ozone-containing reactant gas does not mix with the chlorine dioxide gas.

The ozone can be reacted with the solid phase chlorite media in the presence of carbon dioxide. The carbon dioxide gas source (a carbon dioxide-containing gas) can be provided by any suitable means as long as carbon dioxide is present in the reactant gas at a minimum threshold amount. For example, carbon dioxide can be derived from a pre-manufactured carbon dioxide gas source stored in a storage vessel, or may be generated on-site. The carbon dioxide can be obtained via distillation from air, or by combustion of carbon-based fuels (e.g., methane, gasoline, diesel, kerosene, propane, coal, wood, or other organic matter). Additionally, the carbon dioxide can be a recycled waste product generated by another reaction.

As discussed above, the carbon dioxide gas source can be added (mixed or otherwise combined) to the ozone gas source prior to introducing the ozone gas source to the solid phase chlorite material, or separately in the reaction vessel or at the point of contact with the solid phase chlorite material, to produce a reactant gas containing both ozone and carbon dioxide. The carbon dioxide gas source can have a carbon dioxide concentration of 1 wt. % or more. For example, the concentration may be in a range preferably of from 10-100 wt. %, and more preferably of from 50-100 wt. %, and more preferably of from 70-100 wt. %, and more preferably of from 90-100 wt. %, and even more preferably of from 95-100 wt. %. The combined reactant gas may include carbon dioxide in a concentration ranging from 0-75 wt. %, from 10-60 wt. %, or from 20-50 wt. %. The weight ratio of carbon dioxide to ozone in the reactant gas may be, for example, from 0:1-25:1, from 0.25:1-15:1, from 0.5:1-10:1, or from 1:1-5:1.

The solid phase chlorite reactant media may include a chlorite salt such as sodium chlorite, ammonium chlorite, potassium chlorite, magnesium chlorite, lithium chlorite, calcium chlorite, or suitable combinations thereof. For example, the chlorite reactant media may contain from 10-99.9% by weight of chlorite salt, from 50-99.9% by weight chlorite salt, from 80-99.9% by weight chlorite salt, and from 90-99.9% by weight chlorite salt.

The chlorite media may be a combination or mixture of the chlorite component and unreactive or inert components. Chlorite salts can be unstable under heat or compression, and it may be beneficial to combine the chlorite with an inert component (a "stabilizer") such as sodium carbonate, sodium bicarbonate, sodium sulfate, sodium chloride, and the like. The chlorite media may also have various impurities. One known impurity is sodium hydroxide. Adjusting the purity of the chlorite media may impact the production rate of chlorine dioxide. For example, an increased purity of the chlorite media may provide an increased production rate of chlorine dioxide.

The production rate of chlorine dioxide may be controlled by adjusting the form and purity of the solid chlorite media. It is known that smaller particles have an increased surface area. Therefore, a smaller particle size of the chlorite media will have a greater reactive surface area, at which ozone may react to produce chlorine dioxide. Thus, the rate of production of chlorine dioxide gas may be controlled by adjusting the particle size of the chlorite media, such that a decrease in particle size will typically increase the production rate of chlorine dioxide and an increase in particle size will decrease the production rate of chlorine dioxide. However, the chlorite media preferably has some granularity so that the reactant and product gases can easily pass by the particles. If the chlorite media is too fine, the media can cause back pressure in the reactor. Therefore, the solid phase chlorite media may be composed of any suitable solid form to achieve the desired production rate of chlorine dioxide. For example, in some embodiments the solid chlorite media may be in block form, granular form, pellets, powdered form, or a suitable combination thereof. In one embodiment, the chlorite media includes chlorite salt granules or pellets having an average particle size in the range of from 0.1 mm to 30 mm, from 1 mm to 10 mm, or from 2 mm to 7 mm.

In an embodiment a system is provided that can include a reaction vessel and a plurality of inlet/outlet valves. The reaction vessel includes at least one reaction chamber. The solid chlorite media is contained within the reaction chamber. The chlorite media can be self-supporting or can be supported on a bed, tray, a series of stacked trays, or the like Ozone gas can be selectively fed from the ozone gas source into the reaction chamber through an inlet/outlet valve, or may be fed together as a gaseous mixture/combination with other gases such as carbon dioxide or oxygen. The ozone-containing gas is directed to contact the solid chlorite media within the reaction chamber to react therewith and produce chlorine dioxide gas.

The chlorine dioxide product gas can have a purity, not including a carrier gas, of higher than 75 wt. %, higher than 90 wt. %, higher than 95 wt. %, and preferably higher than 99 wt. %, 99.5 wt. %, or 99.9 wt. %. In other words, unlike aqueous chlorite solutions that are reacted to produce aqueous chlorine dioxide, embodiments of this disclosure provide reactions with very small amounts of unwanted byproducts in the product stream The chlorine dioxide can be produced at any desired rate that is supported by the reaction including, e.g., from 1 mg to 100 kg per hour, from 10 mg to 10,000 mg per hour, or from 100 mg to 1,000 mg per hour. According to embodiments of this disclosure, chlorine dioxide can be produced at approximately a tenth of the cost of commercially available chlorine dioxide solutions The chlorine dioxide gas can be mixed with a carrier gas prior to siphoning from the reaction chamber into a receiving stream or a liquid storage media. The carrier gas may be carried over from the ozone-containing reactant gas. Typical carrier gases that may be suitable include helium, nitrogen, oxygen, argon, hydrogen, air, or mixtures thereof. Chlorine dioxide gas can be volatile in amounts over about 8 wt. %, and thus carrier gas is preferably included in the product gas in amounts so that the absolute concentration of chlorine dioxide is less than 5 wt. %, and preferably in amounts of from 10 ppm to 5,000 ppm, or from 100 ppm to 1,000 ppm.

The chlorine dioxide product gas can be siphoned from the reaction chamber through one of the inlet/outlet valves directly into a receiving stream (e.g., a stream in an industrial process) or into a liquid storage media. The liquid storage media can be in the form of any suitable liquid capable of dissolving the gaseous chlorine dioxide. For example gaseous chlorine dioxide can be dissolved in water and maintained in a storage tank for later use. The chlorine dioxide can be present in the liquid media at concentrations ranging from 50 to 6,000 mg/L, from 500 to 5,000 mg/L, and from 1,500 to 4,000 mg/L. Chlorine dioxide has disinfectant capabilities in water as low as 0.1 ppm for example, and thus the liquid media can be diluted so that the chlorine dioxide is present in useful amounts, e.g., from 0.1 mg/L to 100 mg/L or from 0.1 mg/L to 10 mg/L. Similarly, the liquid media or the product gas can be added to a receiving stream so that the chlorine dioxide is present in the stream at concentrations ranging from 0.1 mg/L to 100 mg/L or from 0.1 mg/L to 10 mg/L.

The chlorine dioxide produced in the reaction may be used to supply high purity chlorine dioxide as a disinfectant. For example the chlorine dioxide can provide:

disinfection of open recirculating cooling and process waters;

disinfection of closed loop cooling and process waters;

disinfection of water in paper making processes;

disinfection of potable water;

disinfection of pool and spa water;

disinfection of ballast water from ships;

disinfection of water used in fruit and vegetable washing;

disinfection of hard surfaces; and disinfection of water used in heat transfer applications such as brewing, pasteurization, canning, and hydrostatic cookers.

The chlorine dioxide can also provide:

destruction of airborne or liquid phase contaminants including cyanide, hydrogen sulfide, carbon disulfide, and mercaptans;

destruction of pathogenic organisms that cause diseases or produce other biological hazards;

replacement of ethylene oxide that is used for medical instrument sterilization or consumer products;

removal of sulfur in kerosene (e.g., by using a liquid composition including from 1,000 to 5,000 mg/L of chlorine dioxide);

fumigants for control of mold and mildew in air ducts, basements, and vapor phase;

fumigants for hatcheries as a replacement of formaldehyde-based fumigants; and chemical selective oxidation.

The reaction system can include a monitoring system that includes a plurality of monitors, controllers, and alarm indicators. The monitoring system is configured to selectively monitor a concentration of ozone in the reactant stream, a concentration of a carrier gas in the reactant stream, a weight of a solid chlorite media, and/or a concentration of chlorine dioxide gas in the product stream or liquid media.

The monitors can be included within the reaction vessel or at selective inlet/outlet valves. The monitors can be configured to take a gas sample from within the system for determining the concentration of the ozone or chlorine dioxide, and can include a scale for measuring the weight of the solid chlorite media. As the solid chlorite media reacts with ozone, its weight decreases.

The monitoring system is configured to analyze the gas sample and generate analytical data as to the nature of the gas sample. Various techniques and equipment can be used for analyzing the gas sample. For example, the monitoring system can measure conductivity, color, pH, dye addition, ion concentration (via ISE), and other parameters for detecting ozone or chlorine dioxide in a solution. The monitoring system can also include a spectrophotometer for measuring chlorine dioxide or ozone both in the gas phase and in solution. Ozone can be measured in gas phase at 260 nm and chlorine dioxide can be measured in a gas phase at 359 nm by UV spectroscopy.

The analytical data obtained by the monitoring system may be used in a step for activating controllers and alarm indicators, such as when the analytical data determines that a reactant or product is present in an amount outside of a predefined threshold value.

The controllers can regulate a gaseous flow rate through each of the inlet/outlet valves. The controllers also control operation of the ozone production generators. For example, the controllers may selectively widen or narrow an opening of a respective inlet/outlet valve to increase or decrease the gaseous flow rate through the respective inlet/outlet valve. The controllers may also selectively operate the ozone generator, for example, by controlling the power source to the ozone generator. The controllers may be manually controlled or automatically controlled such as through a computer processor. For example, a measurement of the concentration of ozone within the system may be used to up-regulate or down-regulate the production of ozone in the ozone production generators, controlling the concentration of ozone provided to the system by the ozone production generators, and thereby controlling the downstream production rate of chlorine dioxide. For instance, if the monitoring system measures a high ozone concentration exceeding a predefined threshold concentration of ozone within the system, the controllers may be actuated to decrease the flow of ozone into the system or to turn off the ozone generators. Alternatively, the alarm indicators may be activated to signal to a user that it is time to perform a specific function.

As one example, the monitoring system could trigger an alarm indicating that the weight of chlorite media is too low or has been consumed so that the user can replace the chlorite column or drum. Optionally, the system can trigger a control operation to add more chlorite media to the reaction vessel. As shown in the examples below, once the chlorite media is consumed beyond a certain threshold, excess ozone gas can actually degrade the chlorine dioxide that is produced. Thus, to provide a consistent and high concentration product stream, it is desirable to ensure that excess chlorite media is present to consume substantially all of the ozone reactant. As an input for this type of control, the concentration of chlorine dioxide in the liquid media can be measured. Once the concentration begins to decline (e.g., by 2 to 30% from its peak concentration, or from 5 to 15% decline from the peak concentration), the system can trigger a control operation or an alarm operation to ensure that more chlorite reactant is added. Also, if a liquid media is used to collect the chlorine dioxide gas, excess ozone will cause the conductivity of the liquid to increase. Thus, the system can monitor the liquid media and trigger an alarm or control operation once the conductivity of the liquid increases beyond a threshold level.

Figure 2:
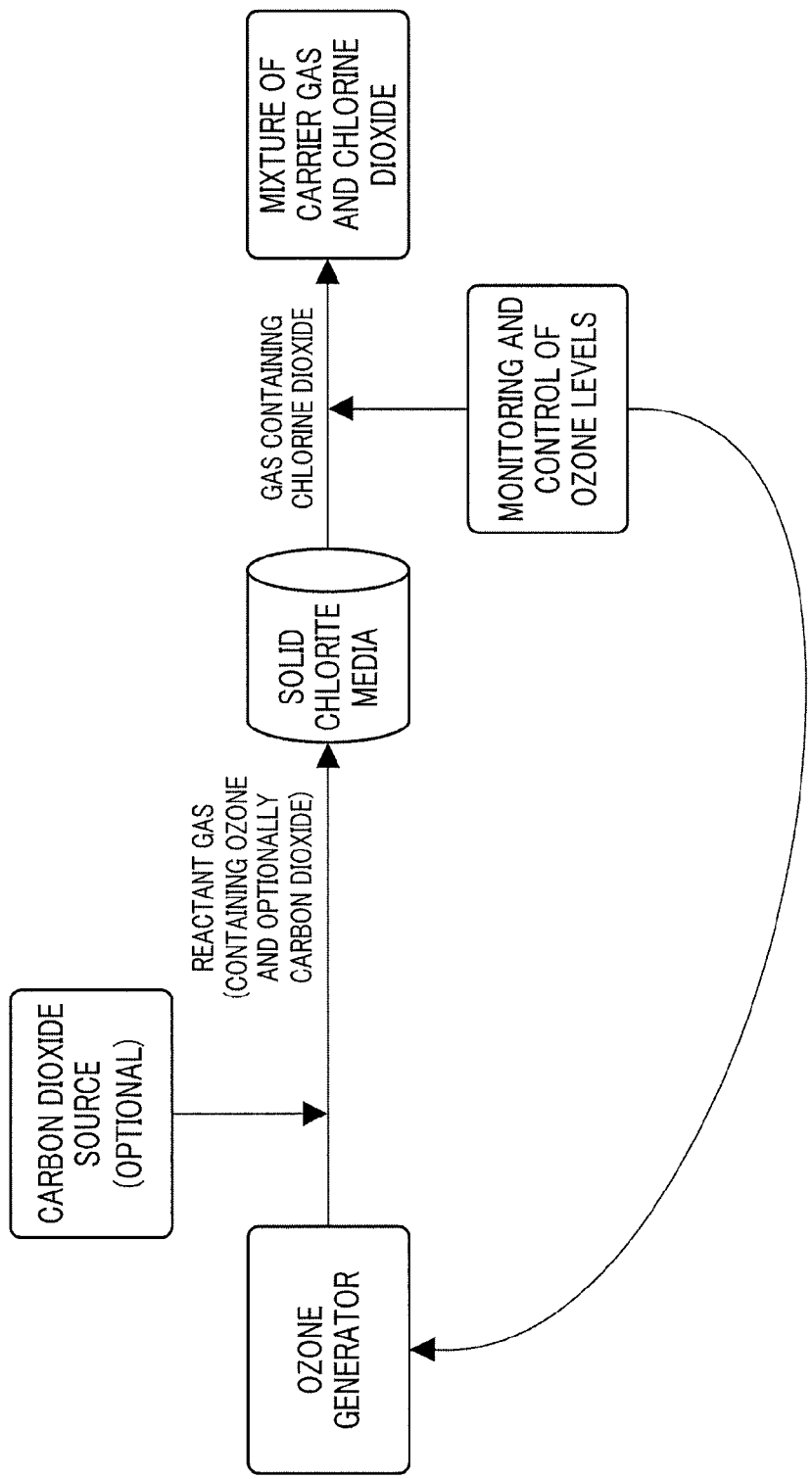
FIG. 2 is a schematic diagram showing a system for producing chlorine dioxide according to embodiments of the disclosure.

An embodiment of the chlorine dioxide system is illustrated in FIG. 2. The system includes an ozone generator, a reaction vessel, and a monitor and controller, each in operational communication. The system can optionally include a carbon dioxide gas source that is coupled to the ozone-containing gas stream. The ozone generator is configured to produce and deliver an ozone gas into a first end of the reaction vessel. The carbon dioxide gas can be combined or mixed with the ozone gas stream (as shown in FIG. 2), or can be separately provided to the reaction vessel. A chlorite media is disposed within the reaction vessel. As ozone (an optionally carbon dioxide) contacts the chlorite media, a chlorine dioxide gas is produced. The chlorine dioxide gas is evacuated out of the reaction vessel at a second end of the reaction vessel into either a liquid storage media or a receiving stream. The monitor and controller are fully integrated with the system and include monitors for the amounts of the chlorine dioxide gas and the ozone gas, and for a weight of the chlorite media. The monitors and controllers can control an ozone gas production rate of the ozone generator, a power supply of the ozone generator, a supply of an oxygen-containing gas source for the ozone generator, a supply of chlorite media in the reaction vessel, and an alarm indicator.

EXAMPLES

The following examples are offered in order to more fully illustrate the invention, but are not to be construed as limiting the scope of the invention.

Example 1

In the following example, an 8 g per hour ozone generator operating at full capacity was used. Using ambient air as a source of oxygen, the ozone generator produced approximately 2 g of ozone per hour. The gaseous ozone was reacted with 5 g of dry sodium chlorite suspended in a plastic tube by passing the gaseous ozone over the sodium chlorite. The reaction occurred at room temperature and was not pressurized. The resulting gas was continuously collected in an aqueous solution and was sampled at various time intervals. The concentration of chlorine dioxide present in each sample was measured. The results according to Table 1 are as follows:

TABLE 1

Chlorine dioxide produced over time using air to produce ozone at 2 g per hour and using 5 g solid sodium chlorite.

| Time (min) | $ClO_2$ (ppm) |
|---|---|
| 0 | 0 |
| 5 | 80 |
| 10 | 113 |
| 16.5 | 132 |
| 20 | 135 |
| 25 | 137 |
| 30 | 147 |
| 40 | 147 |
| 50 | 141 |
| 60 | 135 |
| 90 | 105 |
| 180 | 50 |
| 240 | 34 |

Example 2

In another example, an 8 g per hour ozone generator operating at full capacity was used. Using a purified oxygen source, the ozone generator produced approximately 8 g of ozone per hour. The gaseous ozone produced by the ozone generator was reacted with 100 g of dry sodium chlorite suspended in a plastic tube by passing the gaseous ozone over the sodium chlorite. The resulting gas was continuously collected in an aqueous solution and sampled at various time intervals. The concentration of chlorine dioxide present in each sample was measured. The results according to Table 2 are as follows:

TABLE 2

Chlorine dioxide production over time using oxygen to produce ozone at 8 g/hr and using 100 g of solid sodium chlorite.

| Time (min) | $ClO_2$ (mg/L) |
|---|---|
| 0 | 0 |
| 5 | 269 |
| 10 | 490 |
| 15 | 688 |
| 20 | 792 |
| 27.5 | 900 |
| 30 | 906 |

As shown above, the amount of chlorine dioxide produced is directly correlated with the amount of sodium chlorite present in the reaction and the concentration of ozone reacted with sodium chlorite.

Table 1 shows that chlorine dioxide production reaches a maximum, after which it is considered that the chlorite media is consumed by the reaction and ozone enters the aqueous solution destroying the chlorine dioxide. Table 2 shows that increasing the starting amount of sodium chlorite in the reaction to 100 g will yield an increased production of chlorine dioxide gas as compared to the 5 g starting amount of sodium chlorite used in the experiment shown in Table 1. Table 2 also shows that increasing the amount of ozone reacted with sodium chlorite will yield increased production of chlorine dioxide as compared to the production of chlorine dioxide produced in Table 1.

Example 3

Another experiment was conducted to analyze chlorine dioxide production.

A very low capacity (spa eclipse) ozonator was used to produce approximately 50-70 mg/hr of ozone using oxygen as a source gas. The ozone was fed to a reactant tube containing over 500 g of stabilized sodium chlorite (sodium chlorite pellets containing an inert material).

Chlorine dioxide was generated from the reaction and captured in one liter of a 2000 mg/L aqueous solution of hydrogen peroxide at pH 10.35. This solution immediately reduced chlorine dioxide to chlorite. The total amount of chlorite measured directly reflects the amount of chlorine dioxide produced since the chlorine dioxide is captured in the solution and does not escape the liquid (in water alone, the chlorine dioxide gas can strip the water). This enables quantification of the amount of chlorine dioxide produced for experimental purposes. Chloride and chlorite levels were measured in this solution over time using ion chromatography. The results are shown in Table 3 below:

TABLE 3

Chlorine dioxide generation measured as a function of chlorite production.

| Time (min) | Chlorite (mg/L) | Chloride (mg/L) |
| --- | --- | --- |
| 0 | 0 | 0 |
| 1 | 0 | 0 |
| 2 | 3.762 | 0.035 |
| 3 | 6.7371 | 0.773 |
| 4 | 8.8841 | 0.0326 |
| 5 | 12.2367 | 0.0353 |
| 10 | 26.2515 | 0.0412 |
| 15 | 40.9311 | 0.0429 |
| 20 | 56.3943 | 0.0497 |
| 25 | 69.27 | 0.0476 |

Figure 3:
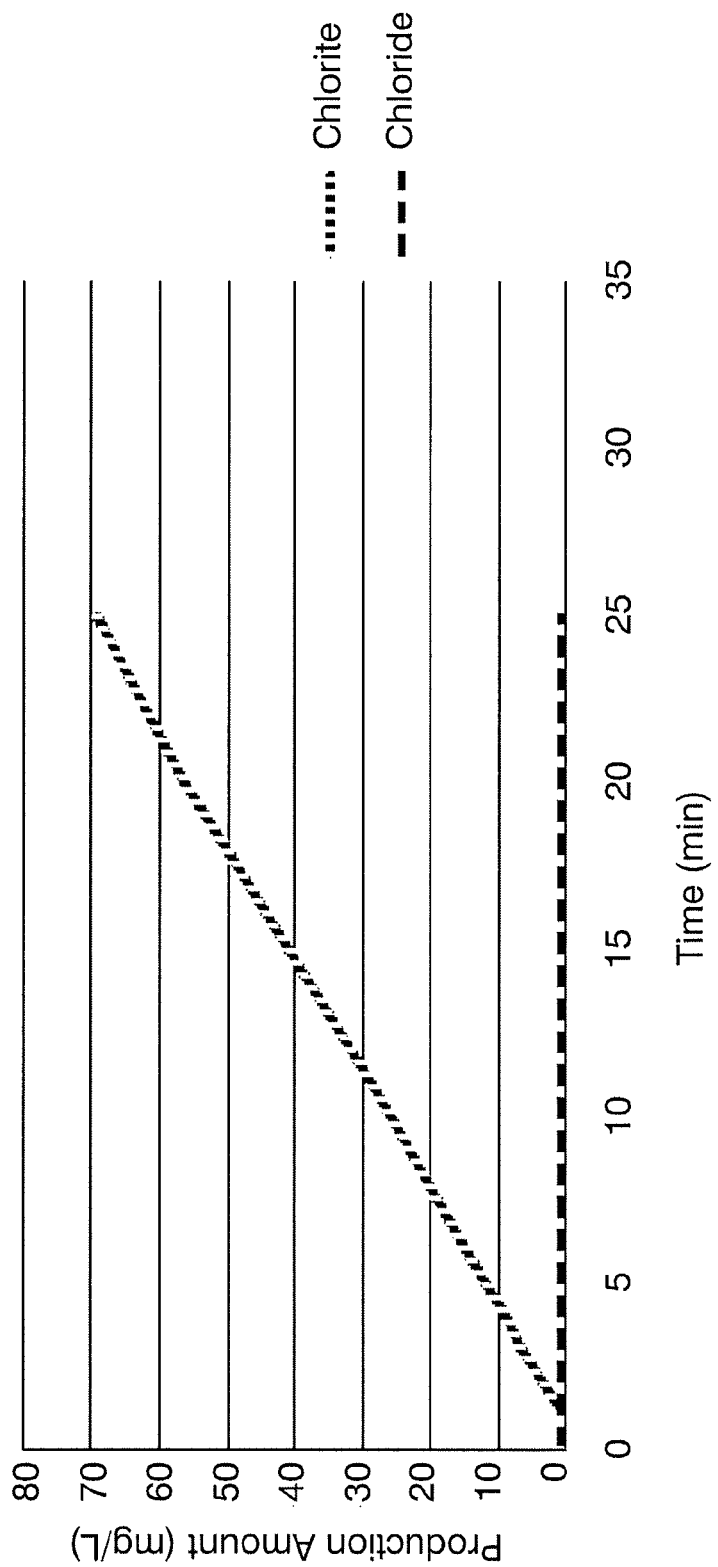
FIG. 3 is a graph showing the rates of chlorine dioxide production (as evidenced by chlorite in the Example 3 experiment)

These results are shown in FIG. 3.

It can be seen from the Example 3 data that production of chlorine dioxide is constant and occurs at a rate of approximately 2.8 mg/L/min. Although this example used a very low capacity ozone generator, even this small device was able to create 4 g of chlorine dioxide per day, which would be sufficient to treat 1,000 gallons of water to a concentration of 1 mg/L. If the chlorine dioxide demand of a system is low, even this experimental set up could be used to treat a 10,000 gallon system to achieve a residual chlorine dioxide of 0.1 mg/L, which would be effective as a biocide. At this rate, 500 g of chlorite would last 125 days before it would need to be replaced.

Chloride is a potential byproduct of the reaction with peroxide, and the very low amounts of chloride demonstrate that this byproduct reaction is not significant. Additionally, there was no chlorate detected. These results demonstrate that the gaseous chlorine dioxide that is produced has a high purity.

Example 4

Another experiment was conducted to analyze the effect of carbon dioxide on the reaction.

Air (containing approximately 23 wt. % oxygen) was introduced to an ozone generator to produce an ozone gas source containing 2 wt. % (20,000 ppm) ozone, as well as components typically found in air (e.g., nitrogen, oxygen, and trace amounts of carbon dioxide). In a control reaction, this ozone gas source was reacted with 100 g of dry, stabilized sodium chlorite (SAF-T-CHLOR, CDG Chemicals) by passing the ozone gas source over the sodium chlorite at a flow rate of 1 standard cubic foot per minute (SCFM).

To determine the effect of carbon dioxide on chlorine dioxide production, carbon dioxide gas containing 99.9 wt. % carbon dioxide was introduced to the ozone gas source at a flow rate of 0.25 SCFM, and the resulting reactant gas was passed over the sodium chlorite. The resulting gas from each reaction was bubbled through a solution of DI water to determine the amount of chlorine dioxide produced. Cumulative measurements were taken in 10 min intervals over the course of 1 hour.

Figure 4:
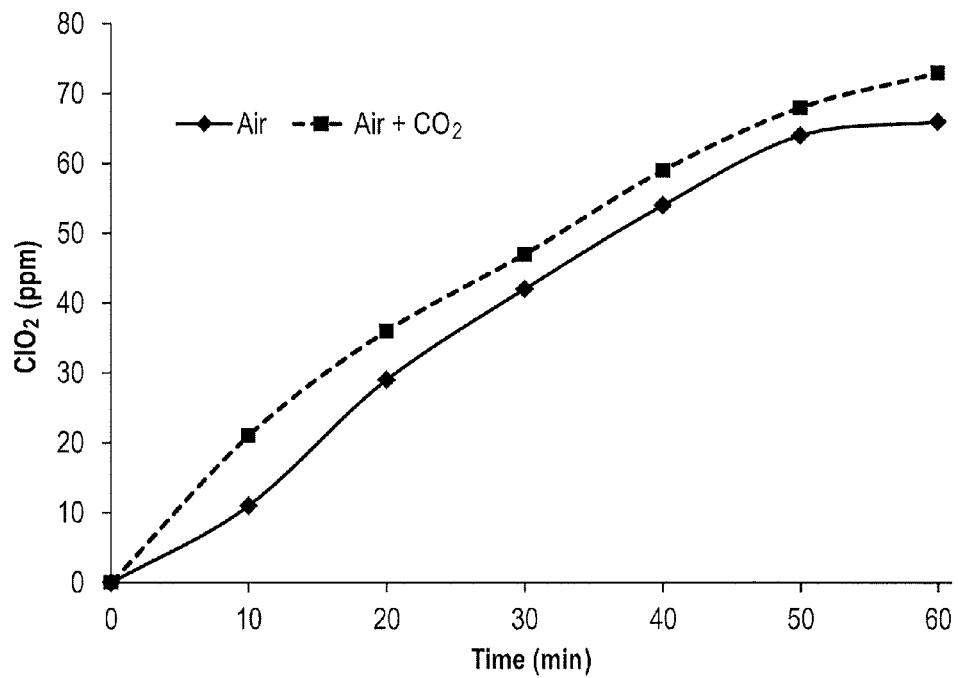
FIG. 4 is a graph showing rates of chlorine dioxide production in the presence of carbon dioxide (as described in the Example 4 experiment)

As shown in FIG. 4, the addition of carbon dioxide to the ozone gas source resulted in an significant increase (approximately 10%) in the amount of chlorine dioxide produced, and the increase persisted throughout the entire experiment.

Example 5

In a similar experiment, an oxygen-containing gas source containing 99.9 wt. % oxygen (as opposed to air) was introduced to the ozone generator to produce an ozone gas source containing about 1-2 wt. % ozone. Chlorine dioxide production was analyzed both in the presence and absence of carbon dioxide according to the methodology set forth above in Example 4.

Because carbon dioxide may affect the pH of the DI water used to capture the chlorine dioxide (and thus the solubility of the chlorine dioxide in the DI water), another sample was studied in which the pH of the DI water was adjusted to eliminate the acidity of the water as a variable. In the control, the ozone gas source was introduced to the sodium chlorite in the absence of carbon dioxide, and the pH of the DI water was adjusted to simulate a solution in which carbon dioxide was present. Specifically, the pH was adjusted to 3.65.

Figure 5:
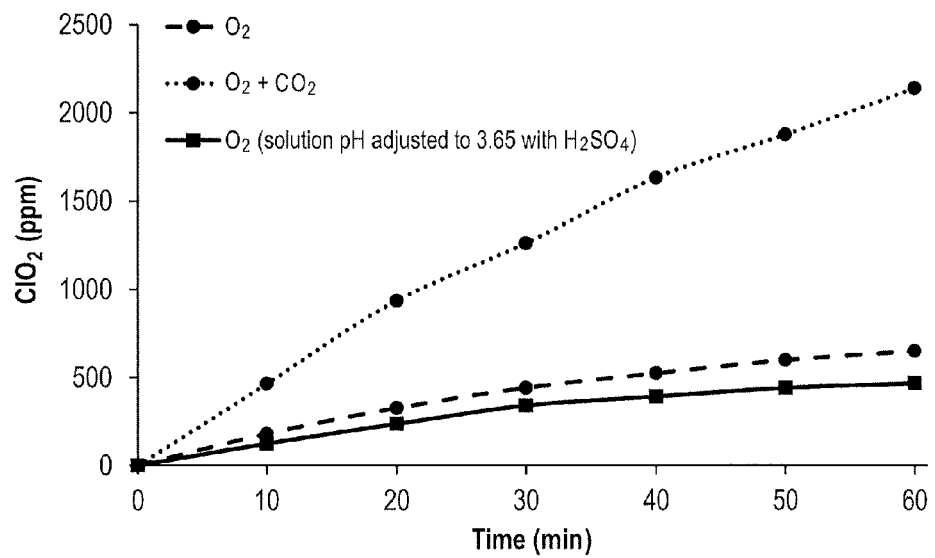
FIG. 5 is a graph showing rates of chlorine dioxide production in the presence of carbon dioxide (as described in the Example 5 experiment)

As shown in FIG. 5, the addition of carbon dioxide to the ozone gas source resulted in a remarkable increase in the amount of chlorine dioxide produced, and the increase persisted throughout the entire experiment. After 1 hour of reaction, the amount of chlorine dioxide produced was approximately four times greater when produced in the presence of carbon dioxide as compared to when produced in the absence of carbon dioxide. Without intending to be bound by theory, it is believed that the increased purity of the oxygen-containing gas source resulted in a greater increase in the amount of chlorine dioxide produced as compared to reaction using air as the oxygen-containing gas source because there were less impurities in the gas to potentially inhibit the formation of ozone.

This difference in chlorine dioxide production was observed even when the DI water was adjusted to 3.65. pH adjustment had little effect on the amount of chlorine dioxide quantified, indicating that the difference in the amount of chlorine dioxide measured was a result of an increase in chlorine-dioxide production as opposed to improved solubility of the chlorine dioxide in the DI water. This suggests that carbon dioxide plays a role in enhancing the reactivity of the sodium chlorite with the ozone.

The results for Examples 4 and 5 are summarized in Table 4 below:

TABLE 4

Cumulative amounts of chlorine dioxide produced after 60 minutes.

| Oxygen Source | $ClO_2$ Production Without $CO_2$ (ppm) | $ClO_2$ Production Without $CO_2$ (pH adjusted) (ppm) | $ClO_2$ Production with $CO_2$ (ppm) | % Increase in $ClO_2$ Production |
|---|---|---|---|---|
| Air | 66 | — | 73 | 10.6 |
| Oxygen | 650 | 467 | 2140 | 358.0 |

Example 6

To determine the effect of different amounts of carbon dioxide on chlorine dioxide production, a similar experiment was conducted where the amount of carbon dioxide in the carbon dioxide gas source was varied. An oxygen-containing gas source containing 99.9 wt. % oxygen was introduced to an ozone generator at a flow rate of 1 SCFM to produce an ozone gas source containing about 1 wt. % ozone. Downstream of the ozone generator, carbon dioxide gas containing 99.9 wt. % carbon dioxide was introduced to the ozone gas source at a flow rate ranging from 0 SCFM (no carbon dioxide gas added) to 0.50 SCFM, as detailed in Table 5 below, to form a combined reactant gas. The resulting reactant gas was passed over 100 g of dry, stabilized sodium chlorite (SAF-T-CHLOR, CDG Chemicals) while maintaining an ozone gas source flow rate of 1 SCFM. The amount of chlorine dioxide produced was measured after 30 min of reaction. Because the ozone gas source flow rate remained constant, the only parameter affecting chlorine dioxide production was the amount of carbon dioxide introduced, as determined by the carbon dioxide gas flow rate.

TABLE 4

Chlorine dioxide generation measured as a function of carbon dioxide gas source flow rate.

| Trial | Oxygen Gas Flow Rate (SCFM) | Carbon Dioxide Gas Flow Rate (SCFM) | Amount of Chloride Dioxide Produced (ppm) |
|---|---|---|---|
| 1 | 1 | 0.00 | 441 |
| 2 | 1 | 0.10 | 748 |
| 3 | 1 | 0.25 | 1260 |
| 4 | 1 | 0.50 | 1126 |

Figure 6:
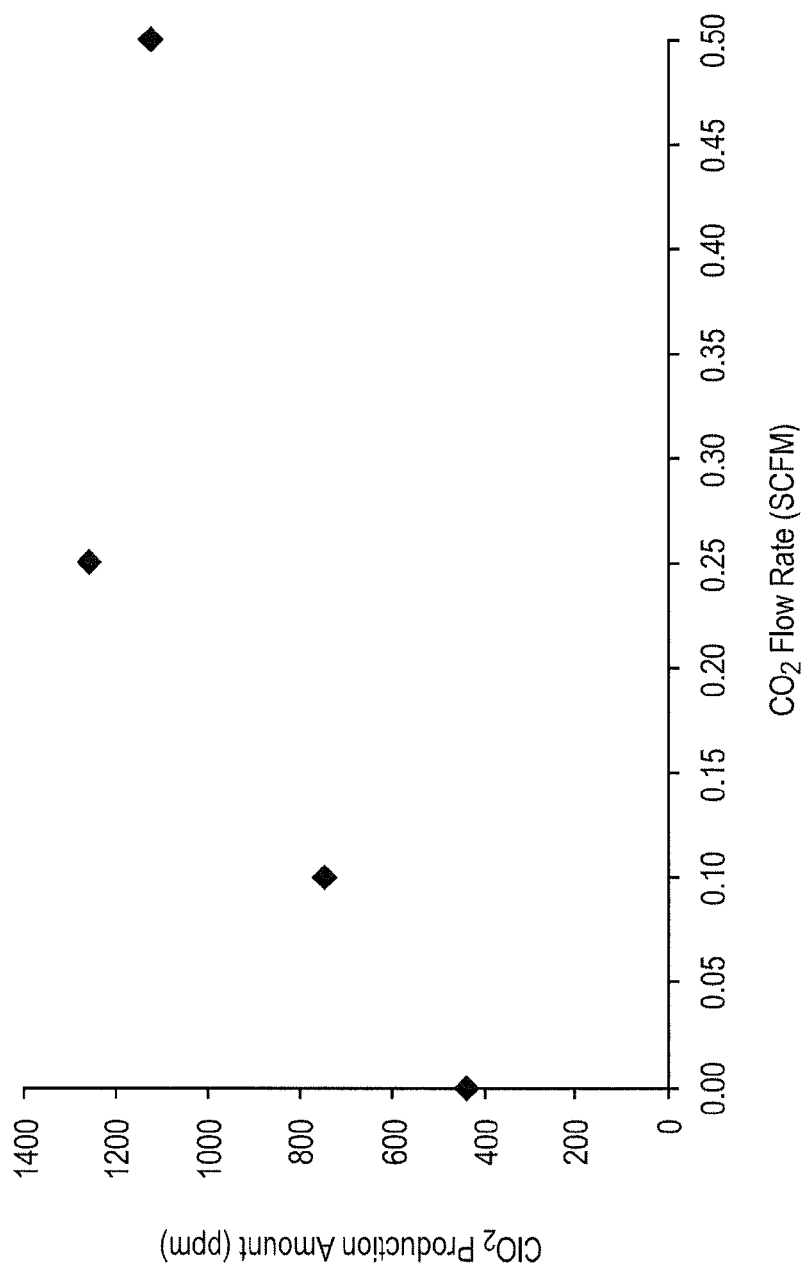
FIG. 6 is a graph showing rates of chlorine dioxide production in the presence of varying amounts of carbon dioxide (as described in the Example 6 experiment).

As shown in FIG. 6, the amount of chloride dioxide produced generally increased as the amount of carbon dioxide introduced into the system increased. This trend was discernible up to a carbon dioxide gas flow rate of 0.25 SCFM, at which the production amount of chloride dioxide was approximately tripled. At a flow rate of 0.5 SCFM, a slight decrease in chloride dioxide production was observed. Although the precise mechanism causing the decrease is unknown, it is believed that the increased flow rate of carbon dioxide above 0.25 SCFM diluted the ozone gas source to the extent that the benefit of adding the carbon dioxide was overcome by the dilution factor.

Although only a few example embodiments have been described in detail above, those skilled in the art will readily appreciate that many modifications are possible in the example embodiments without materially departing from the disclosed embodiments. Accordingly, all such modifications are intended to be included within the scope of this disclosure as defined in the following claims.

What is claimed is:

1. A method of producing gaseous chlorine dioxide, the method comprising:
    contacting a dry chlorite reactant with an ozone-containing gas; and
    reacting the ozone in the ozone-containing gas with the dry chlorite reactant at a gas-solid interface between the ozone-containing gas and the dry chlorite reactant to produce the gaseous chlorine dioxide.

2. The method of claim 1, wherein the dry chlorite reactant is sodium chlorite.

3. The method of claim 1, wherein the ozone-containing gas includes ozone in an amount ranging from 10 ppm to 100,000 ppm.

4. The method of claim 1, wherein the gaseous chlorine dioxide is at least 95 wt. % pure, not including any carrier gas.

5. The method of claim 1, further comprising generating the ozone-containing gas by feeding an oxygen-containing gas into an ozone generator.

6. The method of claim 1, further comprising dissolving the gaseous chlorine dioxide in a liquid media.

7. The method of claim 1, further comprising combining the gaseous chlorine dioxide with a receiving stream of an industrial process.

8. The method of claim 1, wherein the dry chlorite reactant is provided in a solid reactant media that also includes an inert component.

9. The method of claim 8, wherein the solid reactant media is provided as pellets having an average particle size in the range of from 1 mm to 10 mm.

10. A system for producing gaseous chlorine dioxide, the system comprising:
    an ozone generator that is configured to produce an ozone-enriched gas; and
    a reactor that: (i) is coupled to the ozone generator and is configured to receive the ozone-enriched gas from the ozone generator, (ii) includes a dry chlorite reactant that is arranged to contact the ozone-enriched gas and react with ozone in the ozone-enriched gas at a gas-solid interface between the ozone-enriched gas and the dry chlorite reactant to produce the gaseous chlorine dioxide, and (iii) is configured to exhaust a gas product that includes the gaseous chlorine dioxide.

11. The system according to claim 10, further comprising a monitor for determining the amount of ozone present in the gas product.

12. The system according to claim 10, further comprising a vessel that receives the gas product, and wherein the vessel contains a liquid media that dissolves the gaseous chlorine dioxide.

13. The system according to claim 12, further comprising a probe that measures the conductivity of the liquid media.

14. The system according to claim 13, further comprising a controller that triggers an alarm when the conductivity of the liquid media exceeds a predetermined threshold value.

15. The system according to claim 10, wherein:
    the reactor comprises a container selected from at least one of a packed bed, a column, and a drum; and
    the dry chlorite reactant is provided in a solid reactant media that is located in the container, the solid reactant media having a form selected from the group consisting of block form, granular form, pellets, powdered form, or combinations thereof.

16. The system according to claim 10, further comprising a monitor for determining the amount of chlorine dioxide gas in the gas product.

17. The system according to claim 12, further comprising a monitor for determining the amount of chlorine dioxide gas in the liquid media that dissolves the gaseous chlorine dioxide.

18. The method according claim 1, wherein the reaction between the ozone and the dry chlorite reactant also produces an ozonide byproduct.

* * * * *